United States Patent
Grewal et al.

(10) Patent No.: US 9,534,056 B2
(45) Date of Patent: Jan. 3, 2017

(54) ENGINEERED TAA ANTIBODY-TNFSF MEMBER LIGAND FUSION MOLECULES

(75) Inventors: Iqbal Grewal, Snohomish, WA (US);
Michael Gresser, Ojai, CA (US);
Sanjay Khare, Palo Alto, CA (US);
Rashid Syed, Thousand Oaks, CA (US)

(73) Assignee: IMMUNGENE INC, Camarillo, CA (US)

( * ) Notice: Subject to any disclaimer, the term of this patent is extended or adjusted under 35 U.S.C. 154(b) by 67 days.

(21) Appl. No.: 14/124,565

(22) PCT Filed: Jun. 6, 2012

(86) PCT No.: PCT/US2012/000275
§ 371 (c)(1),
(2), (4) Date: Dec. 6, 2013

(87) PCT Pub. No.: WO2012/170072
PCT Pub. Date: Dec. 13, 2012

(65) Prior Publication Data
US 2014/0105860 A1    Apr. 17, 2014

Related U.S. Application Data

(60) Provisional application No. 61/520,248, filed on Jun. 6, 2011.

(51) Int. Cl.
*C07K 19/00* (2006.01)
*C07K 14/525* (2006.01)
(Continued)

(52) U.S. Cl.
CPC ......... *C07K 16/2887* (2013.01); *A61K 38/191* (2013.01); *A61K 38/212* (2013.01);
(Continued)

(58) Field of Classification Search
None
See application file for complete search history.

(56) References Cited

U.S. PATENT DOCUMENTS 7,101,947 B2 * 9/2006 Schlenoff .............. C07B 57/00
7,101,974 B2 * 9/2006 Dahiyat .............. C07K 14/525
(Continued)

FOREIGN PATENT DOCUMENTS

| WO | 9208495 A2 | 5/1992 |
| WO | 2006115800 A2 | 11/2006 |
| WO | 2008124086 A1 | 10/2008 |

OTHER PUBLICATIONS

Cate et al., A novel AML-selective TRAIL fusionprotein that is superior to Gemtuzumab ozogamicin in terms of in vitro selectivity, activity and stability, Leukemia, 23:1389-1397, 2009.*
Liu et al., Recombinant single-chain antibodyfusion construct targeting human melanoma cells and containing tumor necrosis factor, Int. J. Cancer, 108:549-557, 2004.*
(Continued)

*Primary Examiner* — Claire Kaufman
(74) *Attorney, Agent, or Firm* — Craig A. Crandall

(57) ABSTRACT

The field of the present invention relates to genetically engineered fusion molecules, methods of making said fusion molecules, and uses thereof in anti-tumor immunotherapies. More specifically, the present invention relates to engineered fusion molecules comprising an antibody (Ab) which can target tumor cells (e.g., RITUXIN®), fused to one or more biologic moieties capable of inducing apoptosis in tumor cells, e.g., tumor necrosis factor super family (TNFSF) member ligands such as TNF-α, CD40L, CD95L (also "FasL/Apo-1L") and TRAIL/Apo-2L. Importantly, the engineered fusion molecules of the present invention retain the death-inducing properties of the biologic moiety at optimum concentrations and with reduced systemic toxicities.

9 Claims, 2 Drawing Sheets

(51) Int. Cl.
    *C07K 16/28*     (2006.01)
    *A61K 38/19*     (2006.01)
    *A61K 38/21*     (2006.01)
    *A61K 39/395*     (2006.01)
    *A61K 45/06*     (2006.01)
    *C07K 14/475*     (2006.01)
    *A61K 38/00*     (2006.01)

(52) U.S. Cl.
    CPC ........ *A61K 39/39558* (2013.01); *A61K 45/06* (2013.01); *C07K 14/525* (2013.01); *A61K 38/00* (2013.01); *C07K 2319/00* (2013.01)

(56) References Cited

U.S. PATENT DOCUMENTS

| | | | |
|---|---|---|---|
| 7,687,461 B2* | 3/2010 | Desjarlais | A61K 38/191 |
| 8,580,267 B2* | 11/2013 | Pedretti et al. | |
| 2002/0081664 A1 | 6/2002 | Lo et al. | |
| 2004/0014948 A1* | 1/2004 | Halkier | C07K 14/525 |
| 2005/0129689 A1 | 6/2005 | Fanslow et al. | |
| 2010/0311948 A1 | 12/2010 | Hua et al. | |
| 2012/0009149 A1* | 1/2012 | Chang et al. | |

OTHER PUBLICATIONS

Dela Cruz et al., Antibody-cytokine fusion proteins: innovative weapons in the war against cancer, Clin Exp Med 4: 57-64, 2004.*
Eldridge et al, Protein Engineering Design & Selection, 22(11):691-698, 2009.

* cited by examiner

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Peptide linker

<400> SEQUENCE: 1

Ser Gly Gly Gly Gly Ser
1               5

<210> SEQ ID NO 2
<211> LENGTH: 157
<212> TYPE: PRT
<213> ORGANISM: Homo sapiens

<400> SEQUENCE: 2

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
```

```
            65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
                100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155
```

ENGINEERED TAA ANTIBODY-TNFSF MEMBER LIGAND FUSION MOLECULES

RELATED PATENT APPLICATIONS

This application is a U.S. National Phase Application pursuant to 35 U.S.C. §371 of International Patent Application PCT/US2012/000275, filed Jun. 6, 2012, which claims priority to U.S. Provisional Application No. 61/520,248, filed on Jun. 6, 2011, each of which is hereby incorporated in its entirety by reference herein.

SEQUENCE LISTING

The instant application contains a Sequence Listing in the form of a "paper copy" (PDF File) and a file containing the referenced sequences (SEQ D NOs: 1 and 2) in computer readable form (ST25 format text file) which is submitted herein. The Sequence Listing is shown using standard three letter code for amino acids, as defined in 37 C.F.R. 1.822.

SEQ ID NO: 1 is the amino acid sequence of a peptide linker.

SEQ ID NO: 2 is an amino acid sequence of a human mature Tumor Necrosis Factor-alpha ("TNF-α") polypeptide.

TECHNICAL FIELD

The field of the present invention relates to genetically engineered fusion molecules, methods of making said fusion molecules, and uses thereof in anti-tumor immunotherapies. More specifically, the present invention relates to engineered fusion molecules comprising an antibody (Ab) which can target tumor cells (e.g., RITUXIN®), fused to one or more biologic moieties capable of inducing apoptosis in tumor cells, e.g., tumor necrosis factor super family (TNFSF) member ligands such as TNF-α, CD40L, CD95L (also "FasL/Apo-1L") and TRAIL/Apo-2L. Importantly, the engineered fusion molecules of the present invention retain the death-inducing properties of the biologic moiety at optimum concentrations and with reduced systemic toxicities, thus improving the therapeutic index of the engineered fusion molecules.

BACKGROUND OF THE INVENTION

Cancer immunotherapy which utilizes tumor antigen-specific, depleting antibodies have been explored with great success (see, e.g., reviews by Blattman and Greenberg, Science, 305:200, 2004; Adams and Weiner, Nat Biotech, 23:1147, 2005). Tumor antigen-specific, depleting antibody therapies deplete tumor cells by, e.g., antibody-directed cellular cytotoxicity (ADCC), complement dependent cytotoxicity (CDC), induction of apoptosis in tumor cells, and recruitment of T cells responding to tumor antigens released upon antibody-mediated tumor lysis. A couple of examples of tumor antigen-specific, depleting antibodies are HERCEPTIN® (anti-HER2/neu mAb) (Baselga et al., J Clin Oncology, Vol 14:737, 1996; Baselga et al., Cancer Research, 58:2825, 1998; Vogal et al. J Clin Oncology, 20:719, 2002) and RITUXIN® (anti-CD20 mAb) (Colombat et al., Blood, 97:101, 2001).

The current tumor antigen-specific, depleting antibody therapies have clearly made a mark in oncology treatment. Unfortunately, as monotherapy the naked antibodies often lack sufficient potency to kill meaningful amounts of tumor and generally work in about 50% of patients and with partial response, as many tumors do not respond to, or relapse after such therapies. As such, there continues to be extensive research directed toward evaluating and improving the response rates associated with such therapies.

Tumor necrosis factor is a rapidly growing superfamily of cytokines ("TNFSF") that interact with a corresponding superfamily of receptors ("TNFSFR"). Since the discovery of tumor necrosis factor-alpha ("TNF-α") about 25 years ago, the TNFSF has grown to a large family of related proteins consisting of over 20 members that signal through over 30 receptors (see, e.g., "Therapeutic Targets of the TNF Superfamily", edited by Iqbal S. Grewal, Landes Bioscience/Springer Science+Business Media, LLC dual imprint/ Springer series: Advances in Experimental Medicine and Biology, 2009). Members of TNFSF have wide tissue distribution and TNFSF ligand-receptor interactions are involved in numerous biological processes, ranging from hematopoiesis to pleiotropic cellular responses, including activation, proliferation, differentiation, and apoptosis. TNFSF member ligand-receptor interactions have also been implicated in tumorigenesis, transplant rejection, septic shock, viral replication, bone resorption and autoimmunity. The particular response depends upon the receptor that is signaling, the cell type, and the concurrent signals received by the cell.

With the exception of lymphotoxin-α("TNF-β") which is produced as a secreted protein, TNFSF proteins are synthesized as type 2 membrane proteins and fold into conserved β-pleated sheet structures that trimerize. These ligands contain a relatively long extracellular domain and a short cytoplasmic region (Gruss and Dower, Blood, 85:3378-3404, 1995). Their extracellular domains can be cleaved by specific metalloproteinases to generate a soluble molecule. In general, cleaved and noncleaved ligands are active as noncovalent homotrimers, although some members can also exist as heterotrimers. Both membrane bound and secreted ligands are expressed by a variety of normal and malignant cell types (Aggarwal, B B. Nat Rev Immunol, 3:745-756, 2003). Since most of TNFSF member ligands are expressed as transmembrane cell surface proteins, it is believed they are acting at a local level.

TNFSFRs are type I membrane proteins characterized by the presence of a distinctive cysteine-rich domain in their extra-cellular portion (Aggarwal et al, Nat Rev Immunol, 3:745-756, 2003). Most TNFSF member ligands bind to one distinct receptor; however some of the TNFSF member ligands are able to bind to multiple TNF receptors (e.g., TRAIL/Apo-2L) is known to bind five receptors (DR4, DR5, DCR1, DCR2 and OPG)), explaining to some extent the apparent disparity in the numbers of TNFSF member receptors and ligands. TNFSFRs exert their cellular responses through signaling sequences in their cytoplasmic regions.

Based upon their cytoplasmic sequences and signaling properties, the TNFSFRs can be classified into three major groups (Dempsey et al., Cytokine Growth Factor Rev, 14:193-209, 2003). The first group includes receptors that contain a death domain (DD) in their cytoplasmic tail. These receptors include CD95, TNFR1, DR3, DR4, DR5 and DR6. Binding of TNFSF member ligands to their DD containing receptors causes complex signaling through adaptor proteins, such as tumor necrosis factor receptor-associated death domain (TRADD), resulting in activation of the caspase cascade and apoptosis of the cell (Kischkel et al., Immunity, 12:611-620, 2000). The second groups of receptors contain one or more TNF receptor-associated factors (TRAF) interacting motifs (TIM) in their cytoplasmic tails.

This group includes TNFR2, CD40, CD30, CD27, LT-βR, OX40, 4-1BB, BAFFR, BCMA, TACI, RANK, NGFR, HVEM, GITR, TROY, EDAR, XEDAR, RELT and Fn14. Ligand binding to TIM containing TNFSFRs induces recruitment of TRAF family members and activation of cellular signaling pathways including activation of nuclear factor-κB (NF-κB), Jun N-terminal kinase (JNK), p38, extracellular signal regulated kinase (ERK) and phospho-inisitide-3 kinase (Darnay et al., J Biol Chem, 274:7724-7731, 1999). The third group of TNF receptor family members does not contain functional intracellular signaling domains or motifs. These receptors include DcR1, DcR2, DcR3 and OPG. Although this group of receptors lacks the ability to provide intracellular signaling, they can effectively act as decoys to compete for ligand binding and block the signaling through other two groups of receptors (Gibson et al., Mol Cell Biol, 20:205-212, 2000).

As stated above, one group of TNFSFRs are death receptors and have the unique ability to transmit an intracellular death signal and TNFSF ligands such as TNF-α, CD40L, CD95L (also "FasL/Apo-1L") and TRAIL/Apo-2L are capable of inducing apoptosis in tumor cells. Because TNF-α receptors are expressed on many tumor cells, TNF-α has been exploited for its antitumor effects. Its use as an anti-cancer agent, however, is limited because of its systemic toxicity (Feinberg et al., J Clin Oncol, 6:1328-1334, 1988). Similar to the use of TNF-α, in vivo use of CD95L is also limited by its lethal hepatotoxicity resulting from massive hepatocyte apoptosis.

SUMMARY OF THE INVENTION

Based on the background above, the present inventors seek to improve upon existing tumor antigen-specific, depleting antibody therapies and upon existing TNFSF-based therapies by providing the next generation of safer and more effective treatments using genetically engineered fusion proteins which empower monoclonal antibodies by fusing them to one or more TNFSF member ligands, or mutants thereof. The antibody-TNFSF member ligand(s) fusion molecules of the present invention combine the specificity of the antibodies to the target antigen with the potent death-inducing properties of the TNFSF member ligand(s). And, importantly, the antibody-TNFSF member ligand(s) fusion molecules exhibit a reduction in the systemic toxicity of the TNFSF member ligand(s), thus providing a monoclonal antibody-based therapy having superior efficacy and safety profile. The antibody-TNFSF member ligand(s) fusion molecules of the present invention provide improved efficacy and safety for the treatment of cancer, inflammation and other autoimmune diseases. As relates to treatment of cancer, the antibody-TNFSF member ligand(s) fusion molecules offer two approaches for killing tumor cells: (i) via ADCC-independent apoptosis; and (ii) via recruitment of effector cells to kill tumor targets.

The preferred antibody-TNFSF member ligand(s) fusion molecules of the present invention will be engineered using the following important design goals and concepts: 1) utilization of full-length monoclonal antibodies; 2) utilization of a TNFSF member ligand(s) (full length or truncated form), or mutant(s) thereof, having optimal receptor affinity and demonstrating improved therapeutic margin; and 3) use of more than one chain of such TNFSF member ligands, or mutants thereof, in the fusion proteins. Improved therapeutic margin is determined by means of targeting (i.e., testing various Ab-TNFSF member ligand fusion molecules that demonstrate reduced TNFSF member ligand activity on non-targeted cells (cells that do not express the antigen recognized by the Ab) as compared to an wtTNFSF member ligand, and then looking for preserved or improved potency of the Ab-TNFSF member ligand fusion molecule on the targeted cells (cells that express the antigen recognized by the Ab). The ability to provide fusion proteins having any or all of items 1)-3) will provide important and much desired advantages as relates to previously described Ab-based therapies, TNFSF-based therapies, or scFvAb-TNFSF fusion-based reports. For example, in an embodiment of the present invention wherein the fusion molecule comprises a full length antibody fused to one or more chains of a TNFSF member ligand having optimal receptor affinity and improved therapeutic margin, said fusion molecule will be set apart from the prior art molecules not only in terms of design, but in terms of its physical properties, its biologic effects and pharmacologic effects.

Various important and specific differences include: a) fusion molecules of the present invention will have higher affinity and higher avidity due to having at least two binding sites for antigen binding; b) fusion molecules of the present invention will bind FcR and FcRn, which adds new biologic and pharmacologic functions, such as improved half-life, ADCC, CDC, ADCP, etc.; c) fusion molecules of the present invention will have different glycosylation patterns and will be much bigger in size, which will make them potentially different in biodistribution properties; d) fusion molecules of the present invention may carry more than one TNFSF member ligand chains, which will closely mimic natural TNFSF receptor/ligand interactions, and will potentially offer superior potency of our fusion proteins; and e) fusion molecules of the present invention will be selectively targeted to the tumor cells via binding to tumor antigen, thus sparing normal cells and tissues, which will result in a local pro-apoptosis signal induced by the TNFSF member ligand. As such, this engineering approach will result in sparing non-targeted cells and reducing the systemic toxicity of TNFSF member ligand while improving the on target effects and the antitumor activity of the antibody.

The approach used by the present inventors to genetically engineer the fusion molecules of the present invention is as follows: 1) prepared various TNFSF member ligands (e.g., TNF-α, CD40L, FasL/Apo-1L and TRAIL/Apo-2L) (full length or truncated), or mutants thereof known to increase the affinity between ligand/receptor complex and others known to decrease the affinity between ligand/receptor complex; 2) prepared an antibody (e.g., anti-CD20 Ab), or mutant thereof, which binds to a tumor targeted antigen; 3) constructed several Ab-TNFSF member ligand fusion molecules (some of which comprise more than one TNFSF member ligand chains or which comprise a second biologic moiety that is not a TNFSF member ligand); 4) systematically tested the resulting fusion molecules at varying doses in vitro to identify those with the best therapeutic margin; and 5) performed in vivo studies using various fusion molecules to identify which combination of TNFSF member ligand receptor affinity and therapeutic margin is optimal for treating in vivo tumors. As relates specifically to step 4), in vitro functional assays are used to determine: a) the ability of the fusion molecules to bind the TNFSF member ligand/receptor complex on non-targeted cells ("off-target"); b) the ability of the fusion molecule to bind cells expressing the antigen targeted by the Ab ("on-target"); c) the ability of the fusion molecule to bind FcRn receptor; d) the TNFSF member ligand bioactivity of the fusion molecules on non-targeted cells; e) the antiproliferative activity of the fusion molecules on targeted cells; and f) the ability of the fusion molecule to induce apoptosis. The resultant Ab-TNFSF member ligand(s) fusion molecules will deliver a potent death signal via binding of the TNFSF member ligand(s) to its counter receptor(s) on the surface of the tumor cell which promotes apoptosis of the tumor cell. And, importantly, as a result of the focused delivery provided by the antibody to the target antigen, the pro-apoptosis signal is expected to occur primarily at the tumor site, thus sparing non-targeted cells and reducing many of the toxic effects of the TNFSF member ligand while enhancing the antitumor activity of the antibody.

As such, one aspect of the present invention is to provide genetically engineered fusion molecules comprising an antibody fused to one or more TNFSF member ligand molecules for treating in vivo tumors. Either the N- or C-terminus (or both) of the targeting antibody heavy or light chain will be genetically fused with the TNFSF member ligand(s). In certain embodiments, the fusion molecule will comprise an antibody which targets a tumor antigen and a TNFSF member ligand molecule attached to the antibody via a peptide linker, said fusion molecule constructed as described herein and as depicted in, e.g., any of the FIGS. 1-2. The resultant fusion molecule will have the ability to selectively induce apoptosis in tumor cells expressing appropriate death domain containing receptors (e.g., CD95, TNFR1, DR3, DR4, DR5 and DR6) that bind to the TNFSF member ligand(s).

Another aspect of the present invention is to provide genetically engineered fusion molecules comprising an antibody fused to an TNFSF member ligand molecules or mutant thereof and fused to a second biologic moiety, e.g., IFN-α or mutant thereof, for treating in vivo tumors. Either the N- or C-terminus of the targeting antibody heavy or light chain will be genetically fused with the TNFSF member ligand(s) or mutant thereof and the other terminus genetically fused with the IFN-α or mutant thereof. In certain embodiments, the fusion molecule will comprise an antibody, a TNFSF member ligand molecule and IFN-α attached to the antibody via peptide linkers, said fusion molecule constructed as described herein and as depicted in, e.g., any of the FIGS. 1-2. The resultant fusion molecule will have the ability to selectively induce apoptosis in tumor cells expressing: appropriate death domain containing receptors (e.g., CD95, TNFR1, DR3, DR4, DR5 and DR6) that bind to the TNFSF member ligand(s); and expressing IFN-αR that binds to the IFN-α.

Another aspect of the present invention is to provide genetically engineered fusion molecules comprising a bispecific antibody fused to one or two biologic moieties (or mutants thereof) for treating in vivo tumors. A bispecific antibody is an antibody that can bind simultaneously to two targets of different structure, i.e., one arm of the antibody binds to one antigen and the other arm binds to a different antigen. In certain embodiments, bispecific antibodies of the present invention can have binding specificities for at least two different epitopes, at least one of which is, for example, a B-cell, T-cell, myeloid-, plasma-, mast-cell or tumor associated antigen. Either the N- or C-terminus (or both) of the targeting bispecific antibody heavy or light chain will be genetically fused with the biologic moieties or mutant thereof. In certain embodiments, the fusion molecule will comprise a bispecific antibody, a TNFSF member ligand molecule and IFN-α attached to the bispecific antibody via peptide linkers, said fusion molecule constructed as described herein and as depicted in, e.g., any of the FIGS. 1-2.

The fusion molecules of the present invention can be produced recombinantly, using technology that is readily scalable, thus representing an improvement over other antibody-drug conjugate systems and technologies that are typically more challenging and expensive to produce. For example, another aspect of the present invention relates to providing efficient and convenient methods for preparing a genetically engineered fusion molecule of the present invention. In certain embodiments, it is preferable to recombinantly express the chimeric moiety as a fusion molecule using recombinant DNA methodology, e.g., 1) creating a DNA sequence that encodes the fusion protein; 2) placing the DNA in an expression cassette under the control of a particular promoter; 3) expressing the fusion protein in a particular host; and 4) isolating the expressed protein. In alternative embodiments, the TNFSF member ligand is conjugated through a peptide linker to the antibody using a method which generally comprises: 1) preparing a TNFSF member ligand molecule, or mutant thereof; 2) preparing an antibody, or mutant thereof; 3) preparing/obtaining a peptide linker; 4) attaching 1) to 2) using said peptide linker to prepare a fusion molecule; and 5) purifying said fusion molecule. It is further understood that the antibody and the TNFSF member ligand molecule can be attached by any number of means well known to those of ordinary skill in the art.

Another aspect of the present invention relates to polynucleotides that encode the genetically engineered fusion molecules of the present invention. In various embodiments the polynucleotide encodes a fusion molecule comprising an antibody attached to a TNFSF member ligand(s). In preferred embodiments, the TNFSF member ligand encoded by the nucleic acid is a death-inducing TNFSF member ligand such as TNF-α, FasL/Apo-1L and TRAIL/Apo-2L, or mutants thereof. In particularly preferred embodiments the TNFSF member ligand encoded by the polynucleotide is TRAIL/Apo-2L. In certain embodiments the antibody encoded by the nucleic acid comprises the CDRs and/or the variable regions for anti-CD20 antibody such as RITUXIN®. In various embodiments the polynucleotide encodes a peptide linker (e.g., SG4S as described herein) attaching the antibody to the TNFSF member ligand(s).

Another aspect of the present invention relates to a pharmaceutical composition, and method of preparing said pharmaceutical composition, wherein said composition comprises the genetically engineered fusion molecule of the present invention as an active ingredient, in a pharmaceutically acceptable carrier.

Another aspect of the present invention relates to a method of treating tumors or tumor metastases in a patient, comprising administering to said patient a therapeutically effective amount (either as monotherapy or as part of a combination therapy regimen) of a genetically engineered fusion molecule of the present invention in pharmaceutically acceptable carrier, wherein such administration promotes apoptosis and tumor regression and/or tumor death.

BRIEF DESCRIPTION OF DRAWINGS

In FIG. 1, the ovals labeled as $V_L$, $V_H$, $C_L$, $C_{H1}$, $C_{H2}$ and $C_{H3}$ represent a full length antibody (Ab) as defined herein. The oval labeled C represents a cytokine, e.g., TNFSF member ligand, or mutant thereof. A linker is represented by the squiggled line. As depicted in FIG. 1, C is attached to the Ab via a linker at the C-terminus at the two $C_{H3}$ sites. In one alternative embodiment, there may be a second C attached to the Ab via a linker at the N-terminus at the two $V_H$ sites or at the two $V_L$ sites. In yet another embodiment, C will be attached to the Ab at either the N-terminus or C-terminus of the Ab heavy or light chain, and will not involve a linker.

In FIG. 2, the ovals labeled as $V_L$, $V_H$, $C_L$, $C_{H1}$, $C_{H2}$ and $C_{H3}$ represent a full length antibody (Ab) as defined herein. The oval labeled C represents a cytokine, e.g., TNFSF member ligand, or mutant thereof. A linker is represented by the squiggled line. As depicted in FIG. 2, C is attached to the Ab via a linker at the N-terminus at the two $V_L$ sites. In one alternative embodiment, C will be attached to the Ab via a linker at the two $V_H$ sites rather than the two $V_L$ sites. In yet another alternative, C will be attached to the Ab via a linker at an internal site rather than at the $C_{H3}$, $V_L$, or $V_H$ sites. In yet another alternative embodiment, there may be a second C attached to the Ab via a linker at the C-terminus at the two $C_{H3}$ sites.

DETAILED DESCRIPTION OF THE INVENTION

Figure 1:
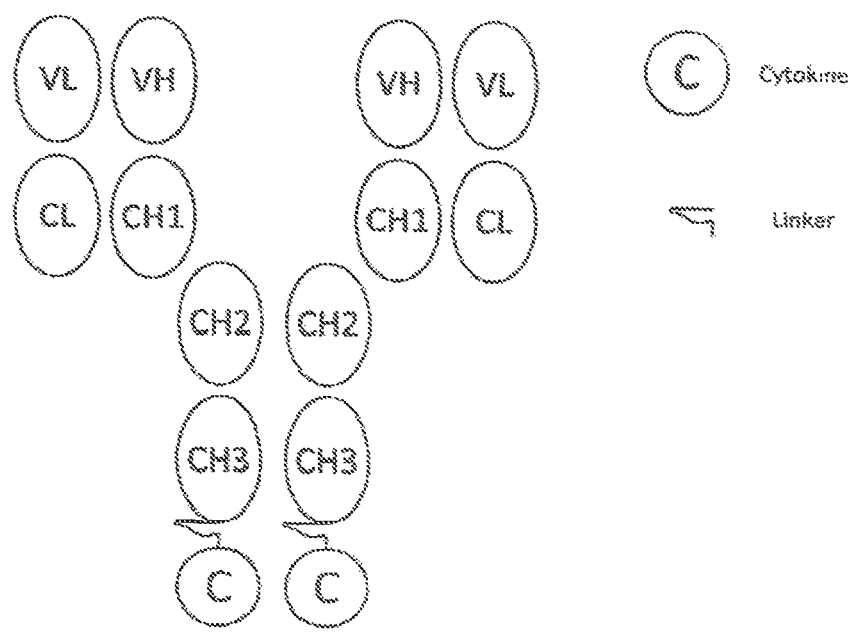
FIG. 1 depicts one proposed design for a genetically engineered fusion molecule of the present invention.

As those in the art will appreciate, the foregoing detailed description describes certain preferred embodiments of the invention in detail, and is thus only representative and does not depict the actual scope of the invention. Before describing the present invention in detail, it is understood that the invention is not limited to the particular aspects and embodiments described, as these may vary. It is also to be understood that the terminology used herein is for the purpose of describing particular embodiments only, and is not intended to limit the scope of the invention defined by the appended claims.

The terms "polypeptide", "peptide" and "protein" are used interchangeably herein to refer to a polymer of amino acid residues. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (amino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether bond as opposed to an amide bond.

The term "isolated" polypeptide or peptide fragment as used herein refers to a polypeptide or a peptide fragment which either has no naturally-occurring counterpart, or has been separated or purified from components which naturally accompany it, e.g., in tissues such as pancreas, liver, spleen, ovary, testis, muscle, joint tissue, neural tissue, gastrointestinal tissue, or body fluids such as blood, serum, or urine. Typically, the polypeptide or peptide fragment is considered "isolated" when it is at least 70%, by dry weight, free from the proteins and naturally-occurring organic molecules with which it is naturally associated.

As used herein, an "antibody" refers to a protein comprising one or more polypeptides substantially or partially encoded by immunoglobulin genes or fragments of immunoglobulin genes and having specificity to a tumor antigen or specificity to a molecule over-expressed in a pathological state. The recognized immunoglobulin genes include the kappa, lambda, alpha, gamma, delta, epsilon and mu constant region genes, as well as subtypes of these genes and myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. The term antibody is used herein in the broadest sense and specifically covers full-length (i.e., naturally occurring or formed by normal immunoglobulin gene fragment recombinatorial processes) monoclonal antibodies, polyclonal antibodies, multispecific antibodies (e.g., bispecific antibodies) and antibody fragments, so long as they exhibit the desired biological activity.

In a full-length antibody, each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$ (and in some instances, $C_{H4}$). Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: $FR_1$, $CDR_1$, $FR_2$, $CDR_2$, $FR_3$, $CDR_3$, $FR_4$. The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online and CDR sequences can be determined, for example, see IMGT/V-QUEST programme version: 3.2.18., Mar. 29, 2011, available on the internet and Brochet, X. et al., Nucl. Acids Res. 36, W503-508, 2008). The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The CDRs are primarily responsible for binding to an epitope of an antigen. The CDRs of each chain are typically referred to as $CDR_1$, $CDR_2$, $CDR_3$, numbered sequentially starting from the N-terminus, and are also typically identified by the chain in which the particular CDR is located. Thus, a $V_H$ $CDR_3$ is located in the variable domain of the heavy chain of the antibody in which it is found, whereas a $V_L$ $CDR_1$ is the $CDR_1$ from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a $C_{H2}$ domain and a $C_{H3}$ domain, and optionally comprises a $C_{H4}$ domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

Antibodies exist as intact immunoglobulins or as a number of well characterized fragments. Such fragments include Fab fragments, Fab' fragments, F(ab)'$_2$ fragments, single chain Fv proteins ("scFv") and disulfide stabilized Fv proteins ("dsFv"), that bind to the target antigen. An "Fv" fragment is an antibody fragment which contains a complete antigen recognition and binding site. This region consists of a dimer of one heavy and one light chain variable domain in tight association. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab, Fab', Fab$_2$, Fab'$_2$, IgG, IgM, IgA, IgE, scFv, dsFv, dAb, nanobodies, unibodies, and diabodies. In various embodiments preferred antibodies include, but are not limited to Fab, Fab$_2$, IgG, IgM, IgA, IgE, and single chain Fv (scFv) antibodies in which a variable heavy and a variable light chain are joined together (directly or through a peptide linker) to form a continuous polypeptide.

In certain embodiments, antibodies and/or fragments used in the constructs of the present invention can be bispecific. A bispecific antibody is an antibody that can bind simultaneously to two targets of different structure. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al., Proc. Natl. Acad. Sci., USA, 78:5807, 1981), by "polydoma" techniques (see, e.g., U.S. Pat. No. 4,474,893), or by recombinant DNA techniques. In certain embodiments bispecific antibodies of the present invention can have binding specificities for at least two different epitopes, at least one of which is, for example, a B-cell, T-cell, myeloid-, plasma-, mast-cell or tumor associated antigen. In various embodiments the antibodies and fragments can also be heteroantibodies. Heteroantibodies are two or more antibodies, or antibody binding fragments (e.g., Fab) linked together, each antibody or fragment having a different specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques previously described (see, e.g., Clackson et al., Nature 352:624-628, 1991; Marks et al., J. Mol. Biol. 222:581-597, 1991). The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "chimeric antibody" as used herein refers to an antibody which has framework residues from one species, such as human, and CDRs (which generally confer antigen binding) from another species, such as a murine antibody that specifically binds targeted antigen.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example, in the CDRs and in particular CDR$_3$. However, the term "human antibody", as used herein, is not intended to include antibodies in which CDR sequences derived from the germline of another mammalian species, such as a mouse, have been grafted onto human framework sequences.

The term "humanized antibody" as used herein refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

The term "recombinant human antibody", as used herein, is intended to include all human antibodies that are prepared, expressed, created or isolated by recombinant means, such as antibodies expressed using a recombinant expression vector transfected into a host cell; antibodies isolated from a recombinant, combinatorial human antibody library; antibodies isolated from an animal (e.g., a mouse) that is transgenic for human immunoglobulin genes; or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. All such recombinant means are well known to those of ordinary skill in the art.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In a preferred embodiment, the antibody mutant will have an amino acid sequence having at least 75% amino acid sequence identity or similarity with the amino acid sequence of either the heavy or light chain variable domain of the species-dependent antibody. Identity or similarity with respect to this sequence is defined herein as the percentage of amino acid residues in the candidate sequence that are identical (i.e., same residue) or similar (i.e., amino acid residue from the same group based on common side-chain properties) with the species-dependent antibody residues, after aligning the sequences and introducing gaps, if necessary, to achieve the maximum percent sequence identity. Preferred antibodies contemplated for use in the fusion molecules of the present invention include depleting antibodies to specific tumor antigens, including, but not limited to, anti-HER2/neu, anti-HER3, anti-HER4, anti-CD20, anti-CD19, anti-CD22, anti-CD33, anti-CD40, anti-CD70, anti-CD123, anti-CD138, anti-CXCR3, anti-CXCR5, anti-CCR3, anti-CCR4, anti-CCR9, anti-CRTH2, anti-PMCH, anti-CD4, anti-CD25, anti-CD200, anti-Grp94 (endoplasmin), anti-BCMA and anti-CD276. All such tumor and inflammatory cell-specific, depleting antibodies have been well described in the literature. In certain preferred embodiments, the antibody is a full-length antibody.

Anti-CD20 Antibodies. The FDA approved anti-CD20 antibody, Rituximab (IDEC C2B8; RITUXAN; ATCC No. HB 11388) has also been used to treat humans. Ibritumomab, is the murine counterpart to Rituximab (Wiseman et al., Clin. Cancer Res. 5: 3281s-6s (1999)). Other reported anti-CD20 antibodies include the anti-human CD20 mAb 1F5 (Shan et al., J. Immunol. 162: 6589-95 (1999)), the single chain Fv anti-CD20 mouse mAb 1H4 (Haisma et al., Blood 92: 184-90 (1998)) and anti-B1 antibody (Liu et al., J. Clin. Oncol. 16: 3270-8 (1998)).

Anti-CD33 Antibodies. CD33 is a glycoprotein expressed on early myeloid progenitor and myeloid leukemic (e.g., acute myelogenous leukemia, AML) cells, but not on stem cells. An IgG.sub.1 monoclonal antibody was prepared in mice (M195) and also in a humanized form (HuM195) that reportedly has antibody-dependent cellular cytotoxicity (Kossman et al., Clin. Cancer Res. 5: 2748-55 (1999)). An anti-CD33 immunoconjugate (CMA-676) consisting of a humanized anti-CD33 antibody linked to the antitumor antibiotic calicheamicin reportedly demonstrated selective ablation of malignant hematopoiesis in some AML patients (Sievers et al., Blood 93: 3678-84 (1999).

Anti-Her-2 Antibodies. The ergB 2 gene, more commonly known as (Her-2/neu), is an oncogene encoding a transmembrane receptor. Several antibodies have been developed against Her-2/neu, including trastuzumab (e.g., HERCEPTIN®); Fornier et al., Oncology (Huntingt) 13: 647-58 (1999)), TAB-250 (Rosenblum et al., Clin. Cancer Res. 5: 865-74 (1999)), BACH-250 (Id.), TA1 (Maier et al., Cancer Res. 51: 5361-9 (1991)), and the mAbs described in U.S. Pat. Nos. 5,772,997; 5,770,195 (mAb 4D5; ATCC CRL 10463); and U.S. Pat. No. 5,677,171.

Anti-Grp94 (endoplasmin) Antibodies. Isolated monoclonal antibodies, including fully human antibodies that specifically bind endoplasmin (Grp94) and use in detecting tumors that express endoplasmin, methods of treatment using the antibodies, and immunoconjugates comprising the antibodies are described in US Patent Application Publication No. 20120009194 (Ferrone et al.).

Anti-CD138 Antibodies. Murine and chimeric anti-CD138 antibodies are described in, e.g., US Patent Application Publication No. 20070183971 (Goldmakher) and 20090232810 (Kraus et al).

Anti-CD70 (CD27L) Antibodies. Antibodies that bind CD70 are described in, e.g., U.S. Pat. No. 7,491,390 (Law et al) and U.S. Pat. No. 8,124,738 (Tenet et al).

Anti-CD40 Antibodies. Antibodies that bind CD40 are described in, e.g., U.S. Pat. No. 7,288,252 (Chu et al), U.S. Pat. No. 7,063,845 (Mikayama et al), and U.S. Pat. No. 7,288,251 (Bedian et al).

Anti-BCMA Antibodies. Antibodies that bind BCMA are described in, e.g., US Patent Application No. 20120082661 (Kalled et al.) and U.S. Pat. No. 7,083,785 (Browning et al).

The term "antigen" as used herein refers to a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least three, and more usually, at least five or eight to ten amino acids in a unique spatial conformation. Methods of determining spatial conformation of epitopes include, for example, x-ray crystallography and 2-dimensional nuclear magnetic resonance.

Tumor antigens expressed on the cell membrane are potential targets in immunotherapy, with the ideal tumor antigen absent on normal cells and overexpressed on the tumor cell surface. As relates to "targeted antigens" contemplated for use herein, particularly preferred targeted antigens include those associated with a hyperproliferative disorder, e.g., cancer. Virtually any antigen may be targeted by the fusion molecules of the present invention, including but not limited to proteins, subunits, domains, motifs, and/or epitopes belonging to the following list of targets: 17-IA, 4-1 BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD86, CD89, CD95, CD123, CD137, CD138, CD140a, CD146, CD147, CD148, CD152, CD164, CD200, CD276, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3C1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, EGAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, HER2, HER2/neu (ErbB-2), HER3 (ErbB-3), HER4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF genetically engineered fusion molecules, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, M195, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-CadHERin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM family members, SLPI, SMAC, SMDF, SMOH, SOD, SPARC, Stat, STEAP, STEAP-II, TACE, TACI, TAG-72 (tumor-associated glycoprotein-72), TARO, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1 CD120a, p55-60), TNFRSF1B (TNF RII CD120b, p'75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-CadHERin, VE-cadHERin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors. The genetically engineered fusion molecules of the present invention may bind one antigen or multiple antigens. In certain preferred embodiments the targeted antigen includes: HER2, HER3, EGF, HER4, B7 family members, the TNFSF members, CD1, CD2, CD3, CD5, CD7, CD13, CD14, CD15, CD19, CD20, CD21, CD23, CD25, CD33, CD34, CD38, CD138, CD200, CD276, Grp94, 5E10, CEA, HLA-DR, HM 1.24, HMB 45, 1a, Leu-M1, MUC1, PMSA, SLAM family members, TAG-72, phosphatidyl serine antigen, and the like. All such antigens have been described in the art.

The TNFSF member ligands specifically contemplated for use in the fusion molecules of the present invention include, but are not limited to, full length and/or truncated forms of tumor necrosis factor-α ("TNF-α"), tumor necrosis factor-β ("TNF-β" or "lymphotoxin-α"), lymphotoxin-β ("LT-β"), CD30 ligand, CD27 ligand, CD40 ligand, OX-40 ligand, 4-1BB ligand, Apo-1 ligand (also referred to as Fas ligand or CD95 ligand), Apo-2 ligand (also referred to as TRAIL, AIM-1 or AGP-1), and Apo-3 ligand (also referred to as TWEAK), APRIL, OPG ligand (also referred to as RANK ligand, ODF, or TRANCE), and TALL-1 (also referred to as BlyS, BAFF or THANK) (see, e.g., "Therapeutic Targets of the TNF Superfamily", edited by Iqbal S. Grewal, Landes Bioscience/Springer Science+Business Media, LLC dual imprint/Springer series: Advances in Experimental Medicine and Biology, 2009; and Aggarwal, BB., Nat Rev Immunol, 3:745-756, 2003), incorporated by reference herein). Among these molecules, TNF-α, TNF-β, CD30 ligand, CD40 ligand, CD70 ligand (also referred to as CD27 ligand), 4-1BB ligand, Fas/Apo1 ligand, TRAIL/Apo-2 ligand and TWEAK/Apo-3 ligand have been reported to be involved in apoptotic cell death. In certain preferred embodiments of the present invention, the TNFSF member ligand is a death-inducing TNFSF member ligand such as TNF-α (Nedwin et al., Nucleic Acids Research, 13 (17) 6361-6373, 1985, FIG. 4) (SEQ ID NO: 2), CD40L (Hollenbaugh et al., EMBO Journal, 11 (12) 4313-4321, 1992), FasL/Apo1 ligand (Suda et al., Cell, 75:1169-1178, 1993) and TRAIL/Apo2 ligand (Wiley et al, Immunity, 3: 673-682, 1995).

Also contemplated for use in the fusion molecules of the present invention are TNFSF member ligand mutants. A TNFSF member ligand mutant comprises a TNFSF member molecule having one or more mutations, wherein the TNFSF member ligand mutant molecule retains TNFSF member ligand function (e.g., its death-inducing properties) when contacted with tumor cells. Single point mutations contemplated for use herein include, but are not limited to, a series of mostly single point mutants (see Table 1 below) that are considered important to the binding affinity of the TNFSF member ligands to their respective TNFSFRs based on published information of their three-dimensional structures, with the assumption that a single point mutation may change the binding affinity but will not completely knock off the activity of the TNFSF member ligand, therefore still retaining, e.g., the death-inducing properties of the TNFSF member ligand, albeit at much higher concentrations.

The present inventors have engineered several fusion molecule constructs comprising an Ab linked to a TNFSF member ligand mutant in order to identify the optimal TNFSF member ligand molecule(s) to be used in the preparation of Ab-TNFSF member ligand mutant fusion molecules which demonstrate improved therapeutic margin as compared to Ab-wtTNFSF member ligand fusion molecules. Specifically, the present inventors seek to identify TNFSF member ligand mutants which will provide for Ab-TNFSF member ligand mutant fusion molecules which demonstrate improved therapeutic margin by means of targeting (i.e., testing various Ab-TNFSF member ligand mutant fusion molecules that demonstrate reduced TNFSF member ligand activity on non-targeted cells (cells that do not express the antigen recognized by the Ab) as compared to an Ab-wtTNFSF member ligand fusion molecule, and then looking for preserved or improved potency on the targeted cells (cells that express the antigen recognized by the Ab).

The approach used to identify such TNFSF member ligand mutants is as follows: 1) we prepared various TNFSF member ligands (e.g., TNF-α, FasL/Apo-1L and TRAIL/Apo-2L) (full length or truncated), or mutants based on structure based modeling thereof known to increase the affinity between ligand/receptor complex and others known to decrease the affinity between ligand/receptor complex; 2) prepared an antibody (e.g., anti-CD20 Ab), or mutant thereof, which binds to a targeted antigen; 3) constructed several Ab-TNFSF member ligand fusion molecules (some of which comprise more than one TNFSF member ligand chains); 4) systematically tested the resulting fusion molecules at varying doses in vitro to identify those with the best therapeutic margin; and 5) performed in vivo studies using various fusion molecules to identify which combination of TNFSF member ligand receptor affinity and therapeutic margin is optimal for treating in vivo tumors. As relates specifically to step 4), in vitro functional assays are used to determine: a) the ability of the fusion molecules to bind the TNFSF member ligand/receptor complex on non-targeted cells ("off-target"); b) the ability of the fusion molecule to bind cells expressing the antigen targeted by the Ab ("on-target"); c) the ability of the fusion molecule to bind FcRn receptor; d) the TNFSF member ligand bioactivity of the fusion molecules on non-targeted cells; e) the antiproliferative activity of the fusion molecules on targeted cells; and f) the ability of the fusion molecule to induce apoptosis.

As described herein and as depicted in Table 1, a single mutation will be identified by the particular amino acid substitution at a specific amino acid position within the full length wild type TNFSF member ligand sequence. For example, a mutation comprising a serine substituted for the full length wild type glutamic acid at amino acid 155 is identified as Glu155Ser. The wild type sequences of the various TNFSF member ligands are well known in the art and publicly available. In addition the mutations depicted in Table 1, additional mutants may also be prepared based on the structure based knowledge of three-dimensional spaces available between the ligand and their respective receptors and the properties of amino acids being changed. For example, in addition to Glu155Ser and Arg158Thr, there may also be Glu155Ala and Arg158Ala mutant made. Such a strategy may be extended to the all the other proposed mutations.

TABLE 1

List of proposed TNFSF Member Ligand Mutant Molecules.

| | | Selection Criteria |
|---|---|---|
| | TRAIL/Apo 2 ligand sequence mutations | |
| M1 | Glu155Ser | Based on Binding Analysis of the TRAIL Ligand-Receptor Complex Structure |
| M2 | Arg158Thr | Based on Binding Analysis of the TRAIL Ligand-Receptor Complex Structure |
| M3 | Tyr189Thr | Based on Binding Analysis of the TRAIL Ligand-Receptor Complex Structure |
| M4 | Ser215Ala | Based on Binding Analysis of the TRAIL Ligand-Receptor Complex Structure |
| M5 | Asp218Thr | Based on Binding Analysis of the TRAIL Ligand-Receptor Complex Structure |
| M6 | Lys224Ser | Based on Binding Analysis of the TRAIL Ligand-Receptor Complex Structure |
| M7 | Tyr237Ala | Based on Binding Analysis of the TRAIL Ligand-Receptor Complex Structure |
| M8 | Leu239Ala | Based on Binding Analysis of the TRAIL Ligand-Receptor Complex Structure |
| M9 | Thr261Ala | Based on Binding Analysis of the TRAIL Ligand-Receptor Complex Structure |
| M10 | Asn262Ser | Based on Binding Analysis of the TRAIL Ligand-Receptor Complex Structure |
| | TNF-α sequence mutations | |
| M11 | His73Ser | Based on Mutational Analysis of TNF-α Complexed to its Receptors |
| M12 | Leu75Ala | Based on Mutational Analysis of TNF-α Complexed to its Receptors |
| M13 | Ser86Ala | Based on Mutational Analysis of TNF-α Complexed to its Receptors |
| M14 | Asn92Ser | Based on Mutational Analysis of TNF-α Complexed to its Receptors |
| M15 | Ile97Ala | Based on Mutational Analysis of TNF-α Complexed to its Receptors |
| M16 | Ser99Thr | Based on Mutational Analysis of TNF-α Complexed to its Receptors |
| M17 | Tyr115Ala | Based on Mutational Analysis of TNF-α Complexed to its Receptors |
| M18 | Phe144Ala | Based on Mutational Analysis of TNF-α Complexed to its Receptors |
| M19 | Glu146Asp | Based on Mutational Analysis of TNF-α Complexed to its Receptors |
| M20 | Ser147Ala | Based on Mutational Analysis of TNF-α Complexed to its Receptors |

In certain embodiments of the present invention, in addition to the TNFSF member ligand(s) or mutants thereof, either the N- or C-terminus of an antibody heavy or light chain will be genetically constructed with one of several other contemplated biologic moieties, e.g., a cytokine or cytokine mutant. The term "cytokine" is a generic term for proteins released by one cell population, which act on another cell population as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-1 and -11; erythropoietin (EPO); osteoinductive factors; interferons such as interferon-alpha, -beta and -gamma colony stimulating factors (CSFs) such as macrophage-CSF (M-CSF); granulocyte macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-10, IL-11, IL-12, IL-13, IL-15, IL-18, IL-23; B7 family members; a tumor necrosis factor such as TNF-alpha or TNF-beta; other polypeptide factors including LIF and kit ligand (KL); and immune inhibitory molecules such as CD200, SLAM family members, and the like. As used herein, the term cytokine includes proteins from natural sources or from recombinant cell culture and biologically active equivalents of the native sequence cytokines. In certain preferred embodiments of the present invention, the cytokine will be an interferon-alpha or an interferon-alpha mutant.

The term "interferon" refers to a full-length interferon or to an interferon fragment (truncated interferon) or an interferon mutant (truncated interferon and interferon mutant collectively referred to herein as 'modified interferon'). Interferons include type I interferons (e.g., interferon-alpha and interferon-beta) as well as type II interferons (e.g., interferon-gamma). The interferon can be from essentially any mammalian species. In certain preferred embodiments, the interferon is from a species selected from the group consisting of human, equine, bovine, rodent, porcine, lagomorph, feline, canine, murine, caprine, ovine, a non-human primate, and the like. In various embodiments the modified interferon comprises one or more amino acid substitutions, insertions, and/or deletions. By "interferon-alpha" or "IFN-alpha" is meant a protein or fragment thereof which can recognize and bind to the IFN-alpha receptor. This includes FDA approved forms of IFN-alpha, such as INF-alpha-2a (Roferon® by Hoffman-LaRoche), INF-alpha-2b (INTRON® A by Schering Corporation) and INF-alpha-n1 (lymphoblastoid interferon called Wellferon® and produced by Wellcome Foundation Ltd—Wellcome Research Laboratories).

Single point mutations contemplated for use herein include, but are not limited to, a series of mostly single point mutants known to increase the affinity between IFN-α and IFN-αR and others known to decrease the affinity between IFN-α and IFN-αR by modeling the changes based on published phage display studies and the NMR structure (Kalie E et al., J. Biol. Chem., 282:11602, 2007; Gomez D and Reich N C, J. Immunol., 170:5373, 2003; Quadt-Akabayov S R et al., Protein Science, 15:2656, 2006; Akabayov S R et al., Biochemistry, 49:687, 2010) with the assumption that a single point mutation may change the binding affinity but will not completely knock off the activity of IFN-α, therefore still retaining the antiproliferative properties albeit at much higher concentrations. This will potentially improve the therapeutic index of the fusion molecules comprising an antibody fused to the interferon-alpha mutants.

The genetically engineered fusion molecules utilized in the current invention are constructed using techniques well known to those of ordinary skill in the art. The fusion molecule may have any of the general constructs as depicted in, e.g., FIGS. 1-2.

Generally speaking, the antibody and TNFSF member ligands of the genetically engineered fusion molecules of the present invention can be joined together in any order. Thus, for example, the TNFSF member ligand can be joined to either the amino or carboxy terminal of the antibody; or conversely, the TNFSF member ligands can be joined to an internal location of the antibody, so long as the attachment does not interfere with binding of the antibody to the target antigen. Alternatively, the antibody can be joined to either the amino or carboxy terminal of the TNFSF member ligands; or joined to an internal region of the TNFSF member ligands. In yet another embodiment, multiple TNFSF member ligands can be joined to either the amino or carboxy terminal, or to an internal region of the antibody.

The present invention thus relates to genetically engineered fusion molecules comprising at least one antibody linked to at least one TNFSF member ligand formed through genetic fusion or chemical coupling. By "linked" we mean that the first and second sequences are associated such that the second sequence is able to be transported by the first sequence to a target cell, i.e., fusion molecules in which the antibody is linked to a TNFSF member ligand via their polypeptide backbones through genetic expression of a DNA molecule encoding these proteins, directly synthesized proteins, and coupled proteins in which pre-formed sequences are associated by a cross-linking agent.

In certain embodiments, the antibody is chemically conjugated to the TNFSF member ligand molecule. Means of chemically conjugating molecules are well known to those of skill The procedure for conjugating two molecules varies according to the chemical structure of the agent. Polypeptides typically contain variety of functional groups; e.g., carboxylic acid (COOH) or free amine (—$NH_2$) groups, that are available for reaction with a suitable functional group on the other peptide, or on a linker to join the molecules thereto. Alternatively, the antibody and/or the cytokine mutant can be derivatized to expose or attach additional reactive functional groups. The derivatization can involve attachment of any of a number of linker molecules such as those available from Pierce Chemical Company, Rockford Ill.

In certain embodiments, the two molecules can be separated by a peptide spacer ("linker") consisting of one or more amino acids. Generally the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity. The term "linker" is thus used to denote polypeptides comprising two or more amino acid residues joined by peptide bonds and are used to link the antibody and biologic molecules of the present invention. Such linker polypeptides are well known in the art (see e.g., Holliger, P., et al., Proc. Natl. Acad. Sci. USA, 90:6444, 1993; Poljak, R. J., et al., Structure, 2:1121, 1994). The choice of linker sequences is based on crystal structure analysis of several Fab molecules. There is a natural flexible linkage between the variable domain and the $C_{H1}/C_L$ constant domain in Fab or antibody molecular structure. This natural linkage comprises approximately 10-12 amino acid residues, contributed by 4-6 residues from C-terminus of V domain and 4-6 residues from the N-terminus of $C_L/C_{H1}$ domain. The N-terminal residues of $C_L$ or $C_{H1}$ domains, particularly the first 5-6 amino acid residues, adopt a loop conformation without strong secondary structures, and therefore can act as flexible linkers between the two variable domains. The N-terminal residues of $C_L$ or $C_{H1}$ domains are natural extension of the variable domains, as they are part of the Ig sequences, therefore minimize to a large extent any immunogenicity potentially arising from the linkers and junctions. Linker length contemplated for use can vary from about 5 to 200 amino acids. In preferred embodiments, the linker may be a proteolysis-resistant linker such as those described in U.S. Publication 20100172868 (Morrison et al.) incorporated by reference herein.

In certain embodiments, the antibody and TNFSF member ligand(s) are linked directly to each other and synthesized using recombinant DNA methodology, e.g., creating a polynucleotide that encodes the antibody-TNFSF member ligand(s) fusion protein, the antibody-TNFSF member ligand(s) mutant fusion protein, a biologically active fragment of the antibody-TNFSF member ligand(s) fusion protein, or functional equivalent thereof; using the polynucleotide to generate recombinant DNA molecules that direct the expression of the encoded fusion protein in a host, and isolating the expressed fusion protein.

In one embodiment of the present invention, nucleic acid sequences encoding the appropriate antibody framework are optionally cloned and ligated into appropriate vectors (e.g., expression vectors for, e.g., prokaryotic or eukaryotic organisms). Such expression vectors, including plasmids, cosmids, and viral vectors such as bacteriophage, baculovirus, retrovirus and DNA virus vectors, are well known in the art (see, for example, Meth. Enzymol., Vol. 185, D. V. Goeddel, ed. (Academic Press, Inc., 1990), and Kaplift and Loewy (Ed.), Viral Vectors: Gene Therapy and Neuroscience Applications (Academic Press, Inc., 1995), each of which are incorporated herein by reference). Additionally, nucleic acid sequences encoding the appropriate TNFSF member ligand(s) or mutants thereof, are optionally cloned into the same vector in the appropriate orientation and location so that expression from the vector produces an antibody-TNFSF member ligand(s) fusion molecule. Some optional embodiments also require post-expression modification, e.g., assembly of antibody subunits, etc. Methods that are well known to those skilled in the art can be used to construct the expression vectors containing the fusion molecule coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

To provide for adequate transcription of the recombinant constructs of the invention, a suitable promoter/enhancer sequence may be incorporated into the recombinant vector. Promoters which may be used to control the expression of the antibody-based fusion protein include, but are not limited to, the SV40 early promoter region (Bernoist et al., Nature 290: 304-310 (1981)), the promoter contained in the 3' long terminal repeat of Rous sarcoma viruses (Yamamoto et al., Cell 22: 787-797 (1980)), the herpes thymidine kinase (tk) promoter (Wagner et al., Proc. Natl. Acad. Sci. USA 78: 144-1445 (1981)), the regulatory sequences of the metallothionine gene (Brinster et al., Nature 296: 39-42 (1982)); prokaryotic expression systems such as the LAC, or β-lactamase promoters (Villa-Kamaroff et al., Proc. Natl. Acad. Sci. USA 75: 3727-3731 (1978)), or the tac lambda phage promoter (DeBoer et al., Proc. Natl. Acad. Sci. USA 80: 21-25 (1983)). Other suitable promoters would be apparent to the skilled artisan.

Additionally, it may be desirable to include, as part of the recombinant vector system, nucleic acids corresponding to the 3' flanking region of an immunoglobulin gene, including RNA cleavage/polyadenylation sites and downstream sequences. Furthermore, it may be desirable to engineer a signal sequence upstream of the fusion molecule-encoding sequences to facilitate the secretion of the fused molecule from a cell transformed with the recombinant vector.

Creation of the fusion molecules can also utilize sequences encoding conservative amino acid substitutions in the biologic moiety sequence, as well as substitutions in the antibody or immunoglobulin region of the fusion protein. Such changes include substituting an isoleucine, valine and leucine for any other of these hydrophobic amino acids; aspartic acid for glutamic acid and vice versa; glutamine for asparagine and vice versa; and serine for threonine and vice versa. Other substitutions can also be considered conservative, depending on the environment of the particular amino acid and its role in the three-dimensional structure of the protein. For example, glycine for alanine can frequently be interchangeable, as well as alanine for valine due to structural and charge similarities.

Cells suitable for replicating and for supporting recombinant expression of fusion protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as E. coli; various eukaryotic cells, such as Chinese hamster ovary cells (CHO), NSO, 293; Yeast; insect cells; hybridomas; human cell lines; and transgenic animals and transgenic plants, and the like. Standard technologies are known in the art to express foreign genes in these systems. The recombinant protein gene is typically operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

Once expressed, the recombinant fusion proteins can be purified by art-suitable techniques such as high performance liquid chromatography, ion exchange chromatography, gel electrophoresis, affinity chromatography, and the like. The actual conditions used to purify a particular protein will depend, in part, on factors such as net charge, hydrophobicity, hydrophilicity, etc., and will be apparent to those having skill in the art. Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

In certain embodiments, the expressed fusion protein may possess a conformation substantially different than the native conformations of the constituent polypeptides and it may thus be necessary to denature and reduce the polypeptide and then cause the polypeptide to re-fold into the preferred conformation. Methods of reducing and denaturing proteins and inducing re-folding are well known to those of skill in the art (see, e.g., Debinski et al., J. Biol. Chem., 268:14065-14070, 1993.

The pharmaceutical compositions of the present invention comprise a genetically engineered fusion molecule of the invention and a pharmaceutically acceptable carrier. As used herein, "pharmaceutically acceptable carrier" means any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof that are physiologically compatible and that do not produce an adverse, allergic or other untoward reaction when administered to a human. Some examples of pharmaceutically acceptable carriers are water, saline, phosphate buffered saline, dextrose, glycerol, ethanol and the like, as well as combinations thereof (see, e.g., Remington's Pharmaceutical Sciences, 18th Ed. Mack Printing Company, 1990, incorporated herein by reference). The preparation of a pharmaceutical composition that contains at least one fusion molecule±an additional active ingredient will be known to those of skill in the art. Id. Moreover, for human administration, it will be understood that preparations should meet specific sterility, pyrogenicity, safety and purity standards as required by FDA Office of Biological Standards.

In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Except insofar as any conventional excipient, carrier or vehicle is incompatible with the genetically engineered fusion molecules of the present invention, its use in the pharmaceutical preparations of the invention is contemplated.

As used herein, the term "administration" refers to the act of giving a drug, prodrug, or other agent, or therapeutic treatment (e.g., radiation therapy) to a physiological system (e.g., a subject or in vivo, in vitro, or ex vivo cells, tissues, and organs). The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. A pharmaceutical composition of the invention is formulated to be compatible with its intended route of administration and therapeutic application. Methods of administering the pharmaceutical compositions of the present invention are via any route capable of delivering the composition to a tumor cell and include, but are not limited to, intradermal, intramuscular, intraperitoneal, intravenous, intratumor, subcutaneous, and the like. As will be appreciated by the skilled artisan, the route and/or mode of administration will vary depending upon the desired results. Typical preferred pharmaceutical compositions are in the form of injectable or infusible solutions, such as compositions similar to those used for passive immunization of humans. In a preferred embodiment, the composition is administered by intravenous infusion or injection. In another preferred embodiment, the composition is administered by intramuscular or subcutaneous injection.

In order to increase the effectiveness of the fusion molecules of the present invention, the pharmaceutical compositions comprising them can be administered in combination with one or more other therapeutic, diagnostic or prophylactic agents. Such additional agents may be included in the same composition or administered separately. Additional therapeutic agents include other anti-neoplastic, anti-tumor, anti-angiogenic or chemotherapeutic agents. Many chemotherapeutic agents are presently known in the art. In some embodiments, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens, and anti-angiogenesis agents. Indeed, in particular embodiments, the fusion molecules of the present invention are employed with one or more chemotherapeutic agents, such as to render effective the chemotherapeutic agent on a resistant cell. The fusion molecules can be used in combination with one or more different cancer treatment modalities, such as radiotherapy, immunotherapy, chemotherapy, gene therapy, surgery, and so forth.

Therapeutic pharmaceutical compositions typically must be sterile and stable under the conditions of manufacture and storage. Sterile injectable solutions can be prepared by incorporating the fusion molecule in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the pharmaceutical compositions active compounds may be prepared with a carrier that will protect the composition against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems (J. R. Robinson, ed., Marcel Dekker, Inc., New York, 1978).

In certain embodiments, the fusion molecules of the present invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the fusion molecules can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the pharmaceutical compositions of the present invention. In certain embodiments, the fusion molecule of the invention is co-formulated with and/or co-administered with one or more additional therapeutic agents. These agents include, without limitation, antibodies that bind other targets, antineoplastic agents, antitumor agents, chemotherapeutic agents, and/or other agents known in the art that can enhance an immune response against tumor cells, e.g., IFN-β1, IL-2, IL-8, IL-12, IL-15, IL-18, IL-23, IFN-γ, and GM-CSF. Such combination therapies may require lower dosages of the fusion molecule as well as the co-administered agents, thus avoiding possible toxicities or complications associated with the various monotherapies.

The pharmaceutical compositions of the invention may include a "therapeutically effective amount" or a "prophylactically effective amount" of the fusion molecule of the invention. As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. The practitioner responsible for administration will, in any event, determine the concentration of active ingredient(s) in a composition and appropriate dose(s) for the individual subject. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present invention will be dictated primarily by the unique characteristics of the active ingredient(s) being used and the particular therapeutic or prophylactic effect to be achieved.

An exemplary, non-limiting range for a therapeutically or prophylactically effective amount of a fusion molecule of the present invention is a dose comprising from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. Usual patient dosages for administration by injection range from about 0.1 to 5 mg/kg/day, preferably from about 0.5 to 1 mg/kg/day. Therapeutically effective serum levels may be achieved by administering multiple doses each day. It is to be noted that dosage values may vary with the type and severity of the condition to be alleviated. It is to be further understood that for any particular subject, specific dosage regimens should be adjusted over time according to the individual need and the professional judgment of the practitioner administering or supervising the administration of the compositions, and that dosage ranges set forth herein are exemplary only and are not intended to limit the scope or practice of the claimed composition.

Another aspect of the present invention relates to a method of treating cancer cells in a patient, comprising administering to said patient a therapeutically effective amount (either as monotherapy or in a combination therapy regimen) of a genetically engineered fusion molecule of the present invention in pharmaceutically acceptable carrier, wherein such administration promotes growth inhibition and apoptosis in a cancer cell. In certain embodiments the cancer cell is a metastatic cell, and/or a cell is in a solid tumor. In certain embodiments the cancer cell is a breast cancer cell. In certain embodiments the cancer cell is a B cell lymphoma, a plasma cell-derived tumor cell, or a myeloid or lymphoid leukemic cell. In certain embodiments the cancer cell is cell produced by a cancer selected from the group consisting of a B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma. In certain embodiments the cancer cell is a leukemia cancer cell or a cell originated from epithelium. In certain embodiments the cancer cell is a cancer cell in a human or in a non-human mammal. In various embodiments the contacting comprises systemically administering the fusion molecule to a mammal. In certain embodiments the contacting comprises administering the fusion molecule directly into a tumor site. In certain embodiments the contacting comprises intravenous administration of the fusion molecule.

The genetically engineered fusion molecules of the present invention are useful in treating disorders characterized as cancer. Such disorders include, but are not limited to solid tumors, such as cancers of the breast, respiratory tract, brain, reproductive organs, digestive tract, urinary tract, eye, liver, skin, head and neck, thyroid, parathyroid and their distant metastases, lymphomas, sarcomas, and leukemias. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophtalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to nasopharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

The following example is provided to describe the invention in further detail.

Example 1

Various engineered fusion molecules comprising one of the various antibodies which can target tumor cells (as described herein) fused to one or more of the various biologic moieties (or mutants thereof) capable of inducing apoptosis in tumor cells (as described herein) can be prepared using the recombinant DNA process for synthesis of a fusion molecule described in the example below.

Figure 2:
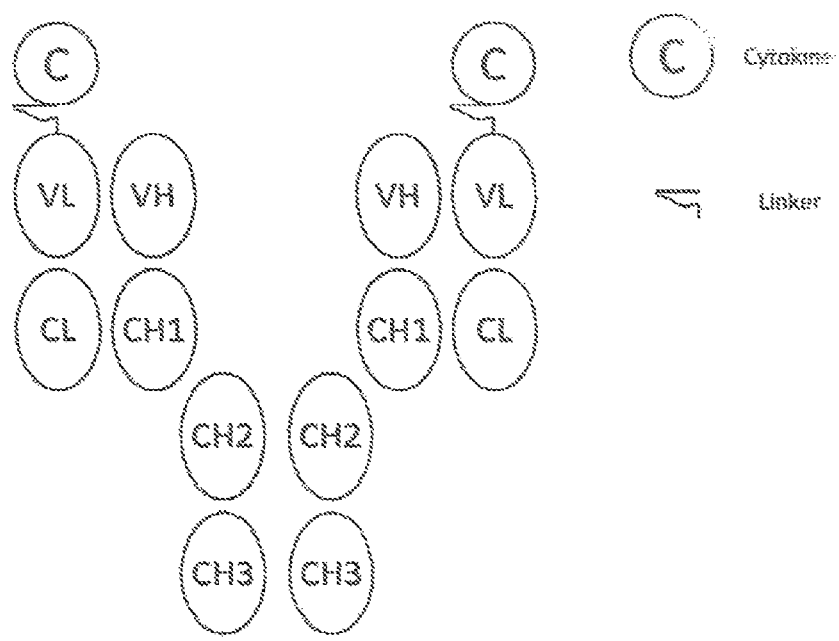
FIG. 2 depicts one proposed design for a genetically engineered fusion molecule of the present invention.

In this example, the FDA-approved anti-CD20 antibody Rituximab (IDEC C2B8; RITUXAN®; ATCC No. HB 11388), the TNFSF member ligand TRAIL (e.g., Wiely et al., Immunity, 3:673-682, 1995), and a proteolysis-resistant linker (as described in U.S. Publication 20100172868 (Morrison et al.)) was used in the preparation a fusion molecule designed as depicted in FIG. 1. The preparation can be generally described as follows: 1) the variable regions for anti-CD20 antibody are amplified and cloned into expression vectors for the production of chimeric antibodies with human kappa light chains and gamma 1 heavy chains; 2) the heavy chain of the antibody was recombinantly engineered with a TNFSF member ligand at the carboxy-terminus using a flexible glycine-serine linker consisting of (SerGly$_4$Ser) (SEQ ID NO: 1); 3) after verifying that the fusion protein vector has the correct nucleotide sequence, it was transfected, along with the light chain vector into NSO cells; 4) transfectants was screened by ELISA for the production of the complete fusion molecule; 5) the clone giving the highest signal was expanded and following sub-cloning was grown in roller bottles; 6) conditioned medium was collected, concentrated, and the protein of interest purified using a single Protein A affinity chromatography step or appropriate alternative chromatography methods. The final product was formulated in a desired buffer and at a desired concentration (the protein concentration is confirmed by UV absorption). The purity of the final product was determined by SDS-PAGE both under reducing and non-reducing conditions. Western blot analysis was used to confirm the expected size of the molecule.

Using the same recombinant DNA processes and methodology, genetically engineered molecules comprising a full-length antibody fused to two biologic moieties, e.g., TRAIL and interferon-alpha IFN-α2a, can be prepared. The molecules may be constructed with one biologic moiety attached via a peptide linker to the C-terminus of the heavy chain of the antibody, and the second biologic moiety attached via a peptide linker the N-terminus of light chain of the antibody.

Example 2

This example describes assays to be used for systematically testing the resulting fusion molecules at varying doses in vitro to identify the ability of the fusion molecules to bind the TNFSF member ligand/receptor complex on non-targeted cells ("off-target"); b) the ability of the fusion molecule to bind cells expressing the antigen targeted by the Ab ("on-target"); c) the TNFSF member ligand bioactivity of the fusion molecules on non-targeted cells; d) the antiproliferative activity of the fusion molecules on targeted cells; and e) the ability of the fusion molecule to induce apoptosis. Again, the example below is specific to the anti-CD20-TRAIL fusion molecule described in Example 1, but the assays can be easily adapted to the other antibodies and biologic moieties taught herein.

Flow Cytometry Analysis for mAb-TNFSF Ligand Fusion Binding to Specific Cells

To determine "off-target" and "on-target" binding ability of the fusion molecules the Daudi cell line, which expresses the CD20 antigen, and a non-CD20 expressing cell line will be incubated with the anti-CD20Ab-TRAIL fusion protein or the control reagents. We will confirm the binding of the fusion protein and compare it with the non-fused mAb. Cells will then be reacted with biotinylated rat anti-human IgG (BD Biosciences), followed by PE-labeled streptavidin (BD Biosciences) and then analyzed by flow cytometry using a FACScan (Becton Dickinson).

TNFSF Member Ligand Bioactivity

The bioactivity of the anti-CD20Ab-TRAIL fusions will be determined by its dose-dependent effects in a well known, standard cytotoxicity assay using cells responsive to TRAIL.

MTS Assay for the Antiproliferative Activity of Fusion Proteins

CD20 expressing lymphoma cells will be plated in a 96-well tissue culture plate at a density of $1.25 \times 10^4$ cells/well and serial dilutions of the fusion molecule added. After 48 hrs at 37° C. in a 5% $CO_2$ atmosphere, plates will be developed by addition of 20 µl of MTS solution (Promega, Madison, Wis.) and measured on an ELISA reader at 490 nm. Percent inhibition of proliferation will be calculated.

$^3$H-Thymidine Incorporation to Measure Antiproliferative Effects

CD20 expressing cells will be plated in a 96-well tissue culture plate at a density of $1.25 \times 10^4$ cells/well and serial dilutions of the fusion molecule added. After 24 hr, [methyl-$^3$H]-thymidine (ICN Biomedicals, Inc., Irvine, Calif.) will be added to a final concentration of 4 µCi/ml. Cells will be cultured for an additional 24 hr and then harvested onto glass fiber filters using a 11050 Micro Cell Harvester, (Skatron, Norway) and counted in a 1205 Betaplate Liquid Scintillation Counter (WALLAC Inc., Gaithersburg, Md.) and the percent inhibition of proliferation calculated.

Inhibition of Proliferation of CFSE Labeled Tumor Cells $1 \times 10^6$ cells will be incubated with 2.5 µM CFSE (Molecular Probes) for 10 min at 37° C. Cells will be then treated with 1 nM of different fusion proteins for 48 hours, and analyzed by flow cytometry following procedures suggested by the manufacturer, using the CellTrace™ CFSE Cell Proliferation Kit (Molecular Probes).

Determination of Apoptosis $1 \times 10^6$ cells will be treated with the fusion molecule for 72 hours. The cells will then be washed with ice-cold PBS. The Annexin V/propidium iodide (PI) assay will be conducted using the Vybrant Apoptosis Assay Kit #2 following procedures suggested by the manufacturer (Molecular Probes).

Example 3

This example describes in vivo studies that can be used to assess the anti-tumor activity of the fusion molecules which demonstrated improved therapeutic margin in the in vitro assays (Example 2) to determine efficacy in treating in vivo tumors. Again, the anti-CD20-TRAIL fusion molecule serves as the example.

Mice (groups of 4) were injected subcutaneously with 5000 CD20-expressing cancer cells on day zero. On days 1, 2 and 3 they were treated intravenously with hepes buffered saline solution (HBSS) or 0.4 µg, 2 µg, or 10 µg of anti-CD20-TRAIL fusion molecules and tumor growth monitored for 20 days.

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A genetically engineered fusion molecule comprising a tumor necrosis factor super family (TNFSF) member ligand mutant attached to a tumor associated antigen (TAA) antibody, wherein said TNFSF member ligand mutant is a mutated tumor necrosis factor-α (TNF-α) consisting of one or more mutations in SEQ ID NO: 2 selected from the group consisting of H73S, L75A, S86A, N92S, I97A, S99T, Y115A, F144A, E146D, and S147A; and wherein said fusion molecule retains the death-inducing properties of said TNFSF member ligand and wherein said fusion molecule when contacted to a tumor cell results in the killing or inhibition of growth or proliferation of said tumor cell.

2. A fusion molecule of claim 1, wherein said TAA antibody is selected from the group consisting of a full-length antibody, chimeric antibody, Fab', Fab, and F(ab')2.

3. A fusion molecule of claim 2, wherein said TAA antibody is a full-length antibody.

4. A fusion molecule of claim 1, wherein said TAA antibody specifically binds a TAA and is selected from the group consisting of anti-HER2/neu, anti-HER3, anti-HER4, anti-CD20, anti-CD19, anti-CD22, anti-CD33, anti-CD40, anti-CD70, anti-CD123, anti-CD138, anti-CXCR3, anti-CXCR5, anti-CCR3, anti-CCR4, anti-CCR9, anti-CRTH2, anti-PMCH, anti-CD4, anti-CD25, anti-CD200, anti-endoplasmin, anti-BCMA and anti-CD276.

5. A fusion molecule of claim 1, wherein said TAA antibody is attached to said TNFSF member ligand mutant with a peptide linker, wherein said peptide linker is fewer than 15 amino acids in length.

6. A fusion molecule of claim 5, wherein said peptide linker is SGGGGS (SEQ ID NO: 1).

7. A pharmaceutical composition comprising a fusion molecule of claim 1 in a pharmaceutically acceptable carrier.

8. A method for the killing or the inhibition of growth or proliferation of a cancer cell in a patient, comprising administering to the patient a therapeutically effective amount of a pharmaceutical composition of claim 7.

9. The method of claim 8, wherein said cancer cell is a cell produced by a cancer selected from the group consisting of a B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system, cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

* * * * *